United States Patent
Kayani

(10) Patent No.: US 8,368,879 B2
(45) Date of Patent: Feb. 5, 2013

(54) SYSTEM AND METHOD FOR THE ULTRASONIC DETECTION OF TRANSPARENT WINDOW SECURITY FEATURES IN BANK NOTES

(75) Inventor: Sohail Kayani, Irving, TX (US)

(73) Assignee: Toshiba International Corporation, Houston, TX (US)

(*) Notice: Subject to any disclaimer, the term of this patent is extended or adjusted under 35 U.S.C. 154(b) by 0 days.

(21) Appl. No.: 13/370,088

(22) Filed: Feb. 9, 2012

(65) Prior Publication Data

US 2012/0140206 A1    Jun. 7, 2012

Related U.S. Application Data

(63) Continuation of application No. 12/556,328, filed on Sep. 9, 2009, now Pat. No. 8,139,208.

(60) Provisional application No. 61/096,212, filed on Sep. 11, 2008.

(51) Int. Cl.
*G01N 21/00* (2006.01)

(52) U.S. Cl. .......................... 356/71; 356/73
(58) Field of Classification Search .............. 356/71–73
See application file for complete search history.

(56) References Cited

U.S. PATENT DOCUMENTS

2006/0151282 A1*   7/2006   Derks et al. .................. 194/207

FOREIGN PATENT DOCUMENTS

JP    09-319918    * 12/1997

OTHER PUBLICATIONS

Derwent translstion of JP 09-319918, Published Dec. 12, 1997.*

* cited by examiner

*Primary Examiner* — Kara E Geisel
(74) *Attorney, Agent, or Firm* — Baker Botts L.L.P.

(57) ABSTRACT

A system and method for automatically detecting the presence of a perforation, tear, or a transparent window security feature in a bank note. The system includes an optical detection device, and an ultrasonic detection device, and a conveyance device for transporting the bank note along a defined path proximate the detection devices. Each detection device comprises a plurality of optical transmitters and corresponding optical receivers that bracket the note path. A computing device is also provided to determine from the output of the optical detection device the presence of an optical abnormality in the bank note; to determine from the output of the ultrasonic detection device the presence of an ultrasonic abnormality in the bank note; and to determine the presence of a perforation, tear, or transparent window feature based upon the results of the optical abnormality determination or the ultrasonic abnormality determination.

17 Claims, 4 Drawing Sheets

SYSTEM AND METHOD FOR THE ULTRASONIC DETECTION OF TRANSPARENT WINDOW SECURITY FEATURES IN BANK NOTES

CROSS-REFERENCE TO RELATED APPLICATIONS

This application is a continuation of U.S. application Ser. No. 12/556,328, filed Sep. 9, 2009, now U.S. Pat. No. 8,139,208 which claims priority to provisional Application No. 61/096,212, filed Sep. 11, 2008, all of which are incorporated by reference herein in their entireties.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates to automated currency processing and, more specifically, to the automated detection of transparent window security features and defects present in polymer bank notes undergoing high-speed processing.

2. Description of Related Art including information disclosed under 37 CFR 1.97 and 1.98

In an effort to combat the counterfeiting of bank notes and other machine-processable security documents, substrate manufactures continue to develop and incorporate new security features into their product. A leap in security technology occurred when polymer substrates were introduced. Polymer bank notes (and some new cotton bank notes) allow security features never before available with traditional cotton-fiber bank notes. One such security feature is the incorporation of a transparent window that penetrates the bank note substrate, sometimes extending to one edge of the note.

Current bank note processing machines feature numerous detectors and sensors to determine various attributes of a bank note being processed. One such detector monitors each note for excessive damage, such as perforations or tears. If the detector senses areas of a note through which light may pass, the note is rejected or even automatically shredded if the processor features note destruction capabilities. This type of action is perfectly suitable for cotton-fiber bank notes which were never intended to have perforations. However, such detection method fails when a bank note having the new window security feature is encountered.

If bank notes having the new transparent window feature were processed by a current high-speed processing machine having perforation defect detection, the machine would sense the intentional transparent window as a hole or perforation and reject the note as damaged. Accordingly, a need exists for a new type of bank note defect detector that can differentiate the transparent window security feature in a polymer or some other substitute note from a perforation. If the transparency is on the edge of the note then the note size calculations are wrong and the machine ability to process the note is compromised as the machine cannot find the leading or the trailing edge of the note being processed causing an erroneous "jam" or stoppage condition.

BRIEF SUMMARY OF THE INVENTION

A system for automatically detecting the presence of a perforation, tear, or a transparent window security feature in a bank note, the system comprising: a conveyance device for transporting a bank note along a defined path; at least one optical detection device, the optical detection device comprising a plurality of optical transmitters proximate one side of the defined path with corresponding optical receivers proximate the other side of the defined path; at least one ultrasonic detection device, the ultrasonic detection device comprising a plurality of ultrasonic transmitters proximate one side of the defined path with corresponding ultrasonic receivers proximate the other side of the defined path; at least one computing device operably coupled with the optical detection device and the ultrasonic detection device, wherein the computing device is capable of executing machine-readable program instructions, the program instructions comprising: determining from the output of the optical detection device the presence of an optical abnormality in the bank note; determining from the output of the ultrasonic detection device the presence of an ultrasonic abnormality in the bank note; and determining the presence of a perforation, tear, or transparent window feature based upon the results of the optical abnormality determination or the ultrasonic abnormality determination.

A method for automatically identifying the presence of a perforation, tear, or transparent window security feature in a bank note, the method steps comprising: transporting the bank note upon a defined path; sensing the bank note with an optical detection device; determining the presence of an optical abnormality based upon the optical detection device output; sensing the bank note with an ultrasonic detection device; determining the presence of an ultrasonic abnormality based upon the ultrasonic detection device output; and determining the presence of a perforation, tear, or transparent window feature based upon the results of the optical abnormality determination or the ultrasonic abnormality determination.

A computer software program tangibly embodied in a computer readable medium, the program including machine-readable instructions executable by a computer processor for performing a method for automatically detecting the presence of a perforation, tear, or transparent window security feature in a bank note being processed by a currency processing machine that utilizes an optical detection device and an ultrasonic detection device to sense the bank note as it advances along a defined path, the program steps comprising: accepting the output from the optical detection device; determining the presence of an optical abnormality on the bank note based upon the optical detection device output; accepting the output from the ultrasonic detection device; determining the presence of an ultrasonic abnormality on the bank note based upon the ultrasonic detection device output; and determining the presence of a perforation, tear, or transparent window feature based upon the results of the optical abnormality determination or the ultrasonic abnormality determination.

These and other improvements will become apparent when the following detailed disclosure is read in light of the supplied drawings. This summary is not intended to limit the scope of the invention to any particular described embodiment or feature. It is merely intended to briefly describe some of the key features to allow a reader to quickly ascertain the subject matter of this disclosure. The scope of the invention is defined solely by the claims when read in light of the detailed disclosure.

BRIEF DESCRIPTION OF THE SEVERAL VIEWS OF THE DRAWING(S)

The present invention will be more fully understood by reference to the following detailed description of the preferred embodiments of the present invention when read in conjunction with the accompanying drawings, in which like reference numbers refer to like parts throughout the views, wherein.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

DETAILED DESCRIPTION OF THE INVENTION classic currency processing machines comprise a bank note feeder device, a transport device or belt along which notes travel past several detectors, and a final disposition component, which comprises typically a pocket for collection of processed notes, a strapper for strapping the notes in bundles, and a means for depositing the notes into the pocket by pulling the notes from the note processing path or transport device. As the note is processed, detectors along the transport path scan the note for various attributes. One such scanner is a note defect detector that checks the notes for damage, such as holes or tears. If sufficient damage is present, the note may be rejected or shredded.

The present invention utilizes a novel method for detecting note defects by differentiating such defects from the transparent window security feature being utilized in new bank note substrates. It is important to note that a perforation is not the same as a transparent window present on, for example, a polymer substrate bank note. The transparent window security features a clear window through which only light will pass. A perforation is a hole through which essentially anything may pass.

Figure 1:
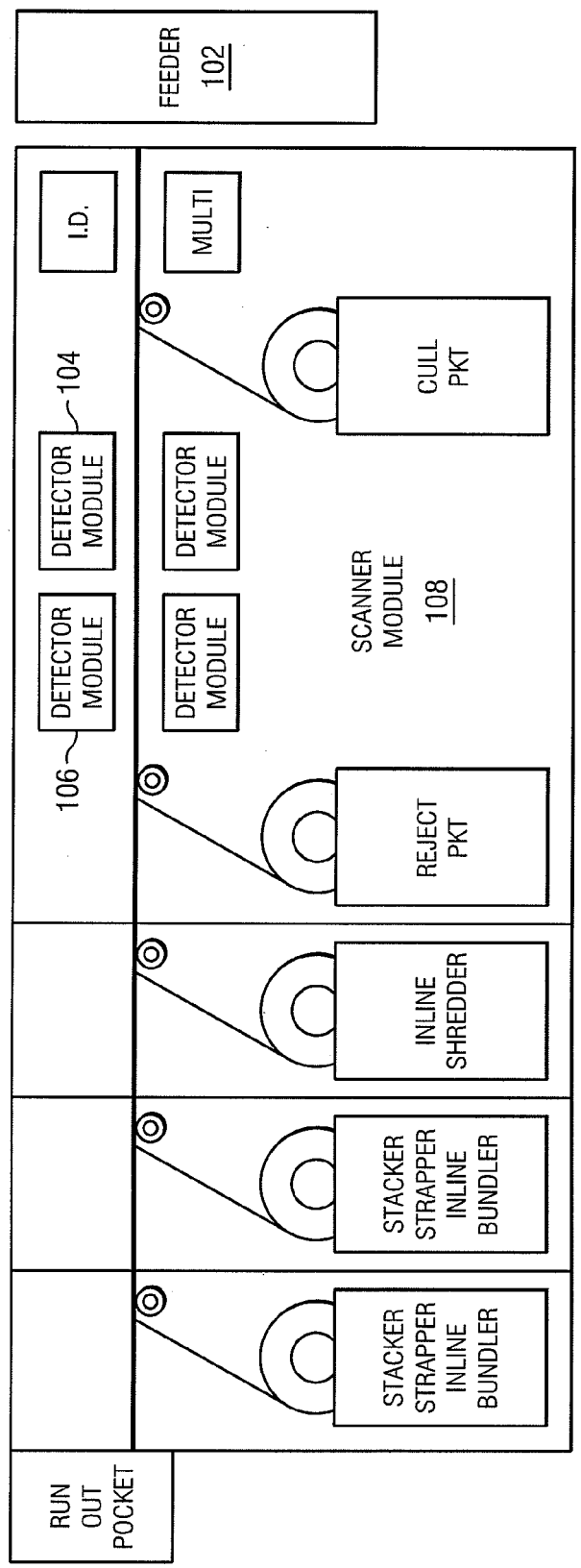
FIG. 1 depicts a block diagram of a basic bank note processing machine, illustrating the location of detectors within the processing stream.

FIG. 1 depicts a block diagram of a bank note processing machine according to the present invention, highlighting the location of the detectors with respect to the processing stream. A bank note is first stripped from a stack of notes in the feeder (102) and sent along the transport path to the scanner module (108). Within the scanner module is an area centered on the transport path in which the detectors are located. In the present embodiment, the note passes the optical detector (104), which checks the note for defects, followed by the ultrasonic detector (106) which makes a similar check. If the note is determined to have a defect, it may be marked for destruction or otherwise removed from the processing stream and placed into a reject pile. While the present embodiment depicts use of a single optical detection device and a single ultrasonic detection device, other embodiments may use multiple instances of each.

The bank note processor can be controlled by multiple computer processing devices, which control the timing of the system as well as activation of the detectors and control of the note disposition. However, one of ordinary skill will appreciate that the central processor may be either a single processing unit or it may consist of multiple processors. Regardless of the configuration, the central computer processor performs a similar function. Computer memory is also present, providing storage capacity for the computer code which controls the processor's actions. The central processor is capable of running the stored program steps from the accessible memory. The processing device may be a dedicated general purpose computer, an embedded RISC or CISC computer processor, a DSP, or the like.

Figure 2A:
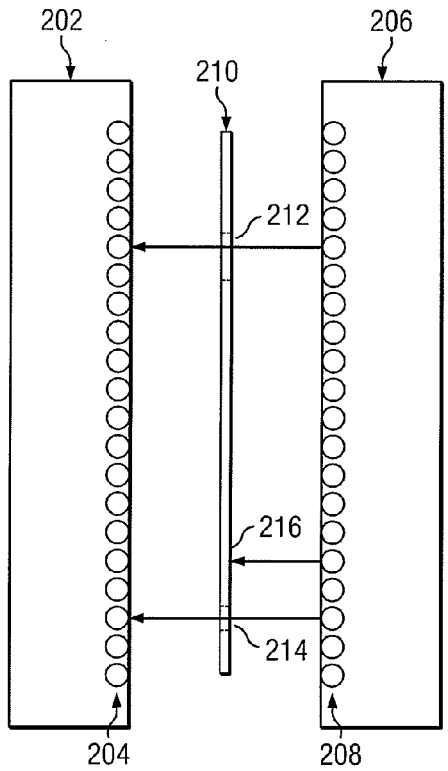
FIG. 2A depicts a close-up view of an optical sensor in additional detail.
Figure 2B:
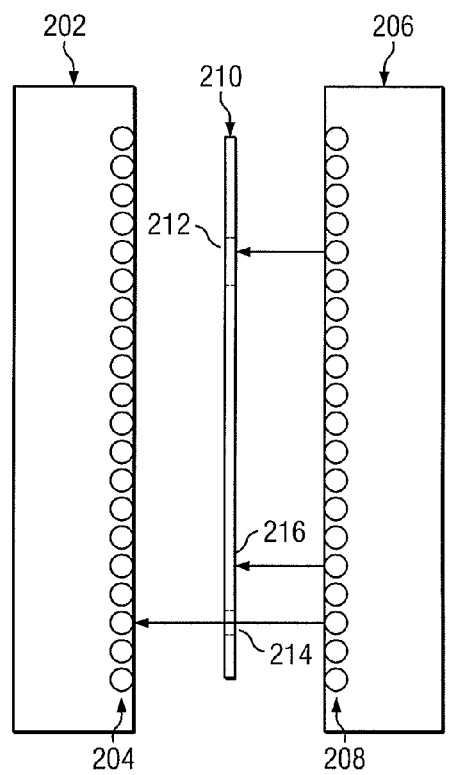
FIG. 2B depicts a close-up view of an ultrasonic sensor in additional detail.

FIGS. 2A and 2B are close-up detailed depictions representative of either an optical detector (104) or an ultrasonic detector (106), respectively. Each type of detector has essentially two sections; a transmitting section (206) and a receiving section (202). Between the sections is the bank note transport path along which the bank note (210) travels.

The transmitter section (206) includes an array of transmitters (208), with each transmitter emitting energy across the bill path. The receiving section (202) includes an array of receivers (204), with each receiver intended to receive the energy emitted from the corresponding transmitter (208). When a bank note (210) is introduced between the receiver sections, the note (210) disrupts the reception of the emitted energy depending upon the features of the note and the type of detector. For example, in the case of an optical detector as depicted in FIG. 2A, the presence of either a transparent window (212) or physical hole (214) will allow the optical energy to pass through the feature (212 and 214) to be sensed by the corresponding receiver (204). However, optical energy will be blocked by the remaining surfaces of the note (216). Conversely, in the case of an ultrasonic detector as depicted in FIG. 2B, the transparent window (212) will block the ultrasonic energy while the physical hole (214) will pass the energy to the corresponding receiver (204).

Figure 3:
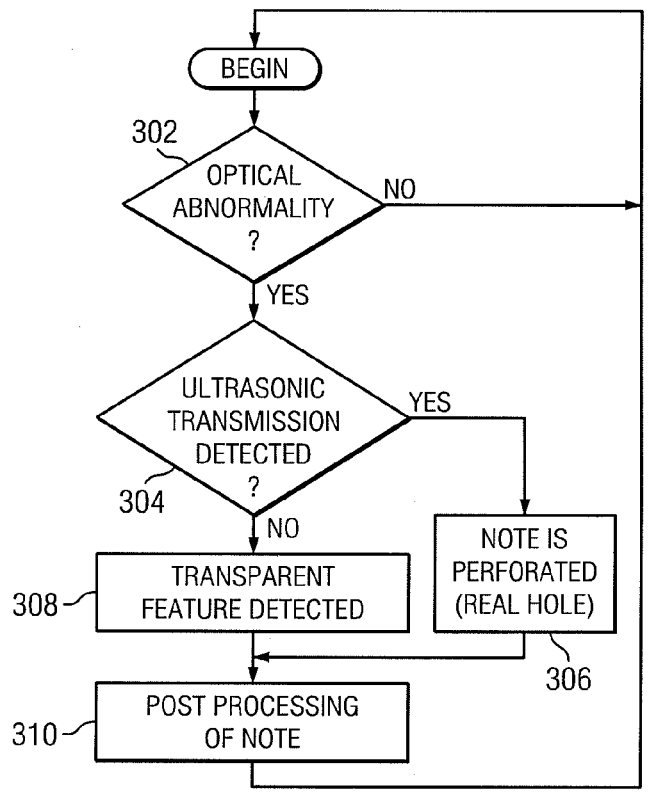
FIG. 3 is a flowchart representing the processing steps.

FIG. 3 provides a flowchart of the processing steps taken by the central processor when sensing a bill in accordance with the present invention. The machine first scans the note using the optical detector to detect an optical abnormality (302). As stated previously, an optical abnormality is present if a perforation or a transparent window is found in the note. The term "abnormality" is used to indicate that such feature (i.e., perforation, tear, or intentionally designed transparent window) is present that would not normally be present in a conventional bank note (see FIG. 4). The transparent window appears to the optical detector as a simple perforation and thus generates the same output. If no optical abnormality is present, then ultrasonic detection is moot. However, if an optical abnormality is present then it is necessary to sense the bill for an ultrasonic abnormality (304).

As stated previously, a transparent window feature is not detected by the ultrasonic detector. Therefore, only a perforation or tear will result in detection of an ultrasonic abnormality. If an ultrasonic abnormality is detected, the system declares the note "perforated" (306) and deals with it accordingly (310). However, if an ultrasonic abnormality is not detected (this following an optical abnormality being detected), then the note is considered to have a transparent window (308) and the note is processed accordingly (310). It is important to note that a transparent window is opaque to an ultrasonic detector because the sound generated is reflected by the transparent window covering. As such, the ultrasonic detector will not "see" the transparent window as a perforation and will generate a different output indicating "no perforation."

FIGS. 4 through 7 depict some of the various bank note transparent window configurations that are serviceable by the present invention. The placement and structure of the transparent window features in the depicted notes is meant to be illustrative only so as to represent the capabilities of the present invention, and are not intended to be exact depictions of transparent window features in actual bank notes that existed as of the filing of this application.

Figure 4:
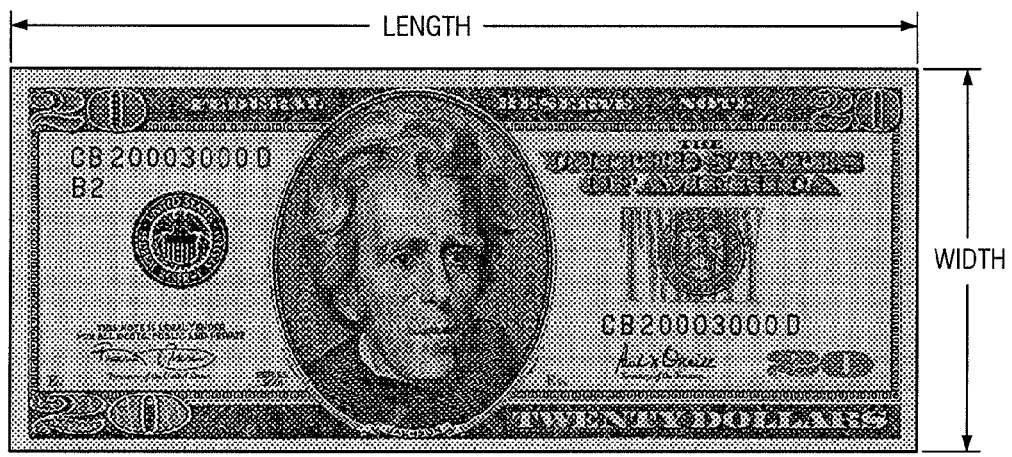
FIG. 4 is a depiction of a standard bank note.
Figure 5:
FIG. 5 is a depiction of a bank note with a transparent window.
Figure 6:
FIG. 6 is a depiction of a bank note with a transparent stripe across the width of the note along one edge.
Figure 7:
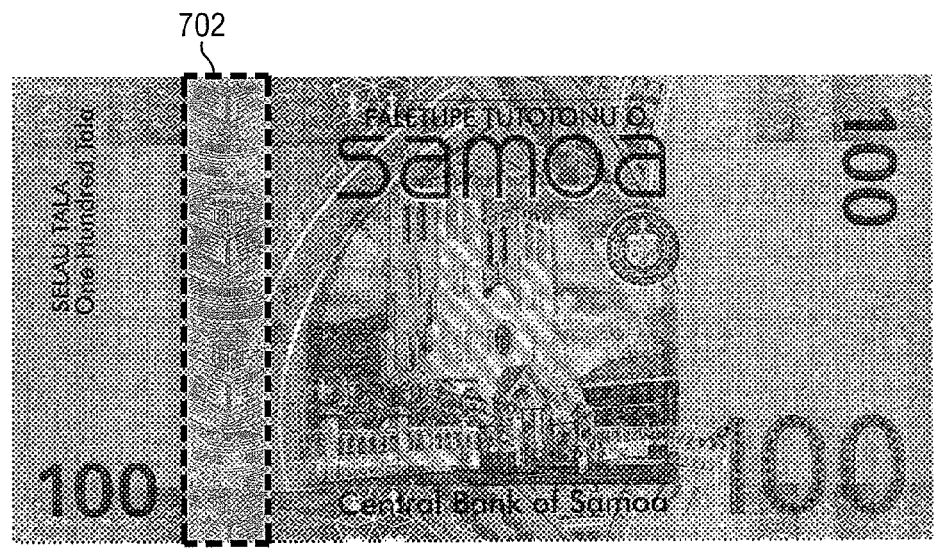
FIG. 7 is a depiction of a bank note with a transparent stripe across the width of the note in a mid location.

FIG. 4 depicts a note that has no transparent window or perforation present in the note body. Such note is readily processed by the present invention as it blocks optical and ultrasonic energy at all points of the note body. FIG. 5 depicts a note that has either a transparent window or a perforation (502). If a perforation, the feature (502) will readily pass either optical or ultrasonic energy. However, if the feature is a transparent window, then optical energy will pass while ultrasonic energy will be blocked. FIGS. 6 and 7 depict notes having a transparent window that spans each note's width. FIG. 6 depicts a note with a transparent window feature (602) that runs the width of the note at one edge of the note. To an optical detector, the note will appear shorter in length than it truly is. However, the ultrasonic detector will see the window as opaque and allow a full length determination. FIG. 7 depicts the transparent window feature (702) located midway along the length. Again, the optical detector will pass energy through this feature (702) while the optical detector will be blocked.

The type of post processing performed on the note (310) varies in accordance with the overall system capabilities. For example, if a note is determined to have a perforation then it may be automatically directed to a note shredder or other disposal means. Also, because a transparent window appears opaque to the ultrasonic detector, it is possible to obtain an accurate measurement of the length of a given banknote— even if the note has a transparent window along the width of the note's edge. The system need only sense the leading edge of the note as it enters detector space and measure the time until the detector senses the trailing edge of the note as it leaves the detector space. The length of the note can then be accurately calculated based upon the linear transport rate of the note with respect to this measured time differential. The width of the bank note can be determined based upon a determination of the number of transmitter/receiver pairs that are blocked by the body of the note in relation to the number of transmitter/receiver pairs that are not blocked by the note. Likewise, a determination can also be made as to the dimensions of the transparent window feature. By sensing, optically, the leading and trailing edges of the transparent window as well as the number of optical detectors that sense the width of the window, it is possible to determine the overall length and width of the window feature. Further, by increasing the number of sensor samples in a given period it is possible to process the data to reconstruct an approximation of the actual transparent window shape.

Although the present embodiment describes obtaining detector readings in a specific order, one skilled in the art will appreciate that the detection sequence may be reversed. For example, the ultrasonic detector may precede the optical detector. Moreover, the detectors may be combined such that the detections occur substantially simultaneously. The sequence of detection is not important. What is important is that both detections occur sufficiently early in the note processing stream such that the machine has time to act upon the detection of a defect.

The invention may be embodied in other specific forms without departing from the spirit or essential characteristics thereof. The present embodiments are therefore to be considered in all respects as illustrative and not restrictive. Accordingly, the scope of the invention is established by the appended claims rather than by the foregoing description. All changes which come within the meaning and range of equivalency of the claims are therefore intended to be embraced therein. Further, the recitation of method steps does not denote a particular sequence for execution of the steps. Such method steps may therefore be performed in a sequence other than that recited unless the particular claim expressly states otherwise.

I claim:

1. A system comprising:
a conveyance device for transporting a bank note along a path;
at least one optical detection device;
at least one ultrasonic detection device;
at least one computing device operably coupled with the optical detection device and the ultrasonic detection device, wherein the computing device is capable of executing machine-readable program instructions, the program instructions comprising:
determining from the output of the optical detection device the presence of an optical abnormality in the bank note;
determining from the output of the ultrasonic detection device the presence of an ultrasonic abnormality in the bank note; and
determining the presence of a transparent window feature based upon the results of the optical abnormality determination and/or the ultrasonic abnormality determination, wherein the presence of a transparent window is determined when an optical abnormality is determined to be present and an ultrasonic abnormality is determined not to be present.

2. The system of claim 1, the program steps further comprising:
processing the bank note in a predefined fashion based upon the presence of an optical abnormality or an ultrasonic abnormality.

3. The system of claim 1 wherein the ultrasonic abnormality determination is performed only in the presence of an optical abnormality.

4. The system of claim 1, the program instructions further comprising:
measuring the transport speed of the bank note; and
determining, using the optical detection device or the ultrasonic detection device, the length of the bank note.

5. The system of claim 4, the program instructions further comprising:
determining, using the optical detection device or the ultrasonic detection device, the width of the bank note.

6. The system of claim 1, the program instructions further comprising:
measuring the transport speed of the bank note; and determining, using the optical detection device or the ultrasonic detection device, the dimensions of a perforation, tear, or transparent window feature present in the bank note.

7. A method comprising:
transporting the bank note upon a defined path;
sensing the bank note with an optical detection device;
determining the presence of an optical abnormality based upon the optical detection device output;
sensing the bank note with an ultrasonic detection device;
determining the presence of an ultrasonic abnormality based upon the ultrasonic detection device output; and
determining the presence of a perforation, tear, or transparent window feature based upon the results of the optical abnormality determination and/or the ultrasonic abnormality determination, wherein the presence of a perforation or tear is determined when both an optical abnormality and an ultrasonic abnormality are determined to be present and wherein the presence of a transparent window is determined when an optical abnormality is determined to be present and an ultrasonic abnormality is determined not to be present.

8. The method of claim 7, further comprising:
processing the bank note in a predefined fashion based upon the presence of an optical abnormality or an ultrasonic abnormality.

9. The method of claim 7 wherein the ultrasonic abnormality determination is performed only in the presence of an optical abnormality.

10. The method of claim 7, further comprising:
measuring the transport speed of the bank note; and
determining, using the optical detection device or the ultrasonic detection device, the length of the bank note.

11. The method of claim 10, further comprising:
determining, using the optical detection device or the ultrasonic detection device, the width of the bank note.

12. The method of claim 7, further comprising:
measuring the transport speed of the bank note; and
determining, using the optical detection device or the ultrasonic detection device, the dimensions of the perforation, tear, or transparent window feature present in the bank note.

13. A computer software program tangibly embodied in a computer readable medium, the program including machine-readable instructions executable by a computer processor for performing a method, the program steps comprising:
determining the presence of an optical abnormality on the bank note based upon signals received from an optical detection device;
determining the presence of an ultrasonic abnormality on the bank note based upon signals received from an ultrasonic detection device; and
determining the presence of a perforation, tear, or transparent window feature based upon the results of the optical abnormality determination and/or the ultrasonic abnormality determination, wherein the ultrasonic abnormality determination is performed only in the presence of an optical abnormality and wherein the presence of a perforation or tear is determined when both an optical abnormality and an ultrasonic abnormality are determined to be present and wherein the presence of a transparent window is determined when an optical abnormality is determined to be present and an ultrasonic abnormality is determined not to be present.

14. The computer software program of claim 13, the program steps further comprising:
processing the bank note in a predefined fashion based upon the presence of an optical abnormality or an ultrasonic abnormality.

15. The computer software program of claim 13, the program steps further comprising:
measuring the transport speed of the bank note; and
determining the length of the bank note using the optical detection device output or the ultrasonic detection device output.

16. The computer software program of claim 15, the program steps further comprising:
determining the width of the bank note using the optical detection device output or the ultrasonic detection device output.

17. The computer software program of claim 13, the program steps further comprising:
measuring the transport speed of the bank note; and
determining the dimensions of the perforation, tear, or transparent window feature present in the bank note based upon the optical detection device output or the ultrasonic detection device output.

* * * * *